United States Patent [19]

McCoy

[11] Patent Number: 4,758,222

[45] Date of Patent: Jul. 19, 1988

[54] STEERABLE AND AIMABLE CATHETER

[76] Inventor: William C. McCoy, 11339 Valley Meadow Dr., Zionsville, Ind. 46077

[21] Appl. No.: 870,926

[22] Filed: Jun. 5, 1986

Related U.S. Application Data

[63] Continuation-in-part of Ser. No. 728,634, May 3, 1985, Pat. No. 4,601,705, which is a continuation-in-part of Ser. No. 547,402, Oct. 31, 1983, Pat. No. 4,543,090.

[51] Int. Cl.⁴ ............................................. A61M 37/00
[52] U.S. Cl. .......................................... 604/95; 128/6; 128/657
[58] Field of Search ................. 604/95, 264, 280, 281; 128/6, 657

[56] References Cited

U.S. PATENT DOCUMENTS

| | | | |
|---|---|---|---|
| 3,043,309 | 7/1962 | McCarthy | 128/343 |
| 3,297,008 | 4/1973 | Berkovits | 128/348 |
| 3,605,725 | 9/1971 | Bentov | 128/2.05 |
| 3,674,014 | 7/1972 | Tillander | 128/2.05 |
| 3,773,034 | 11/1973 | Burns et al. | 128/2 |
| 3,890,977 | 6/1975 | Wilson | 128/418 |
| 4,146,019 | 3/1979 | Bass et al. | 128/6 |
| 4,176,662 | 12/1979 | Frazer | 128/6 |
| 4,456,017 | 6/1984 | Miles | 604/95 |
| 4,543,090 | 9/1985 | McCoy | 604/95 |
| 4,586,923 | 5/1986 | Gould et al. | 128/657 |
| 4,601,705 | 7/1986 | McCoy | 604/95 |

Primary Examiner—Stephen C. Pellegrino
Assistant Examiner—Ralph Lewis
Attorney, Agent, or Firm—Barnes & Thornburg

[57] ABSTRACT

A catheter or the like is steerable through cavities within a body and aimable toward organ or tissue within the body. The catheter includes an elongated tubular member having a distal end for insertion into the body and a temperature-activated memory element in the distal end of the hollow tubular member. The memory element has an initial shape and moves to assume a predetermined shape when heated to a predetermined temperature. A control system is provided for selectively heating the memory element to the predetermined temperature so that the memory element is moved in a first direction to deflect the distal end of the tubular member and thereby steer or aim the catheter within the body. A spring assembly is provided for yieldably urging the memory element in an opposite second direction to establish the initial shape and also to aid in returning the memory element to its initial shape when the temperature of the memory element is less than the predetermined temperature. The spring assembly includes a core member for supporting the memory element and a resilient member. Both the core member and resilient member are preformed to assume curved shapes and both move to assume a shape other than the preformed curved shapes in response to movements of the memory element in the first direction.

30 Claims, 3 Drawing Sheets

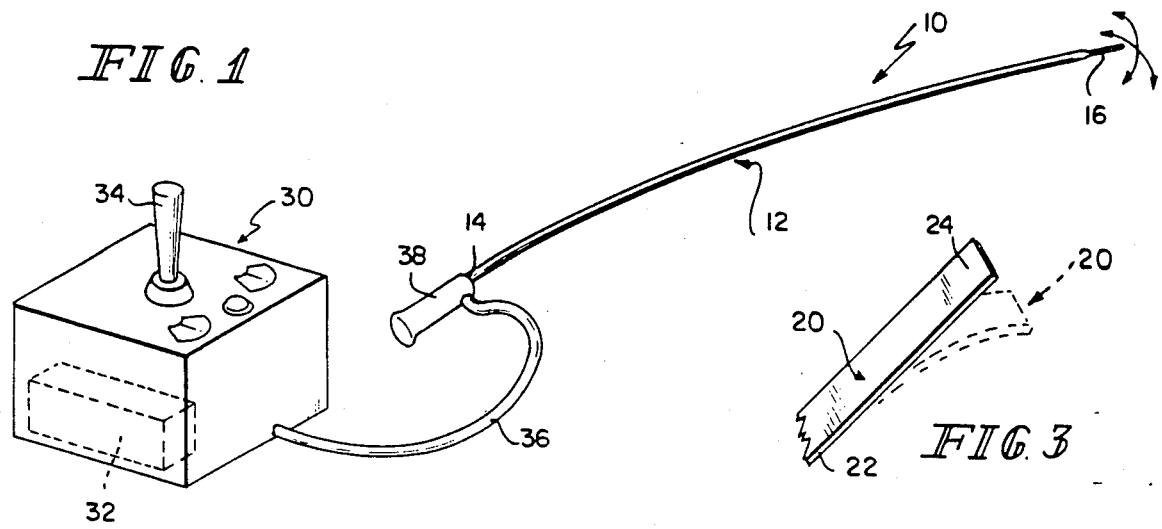
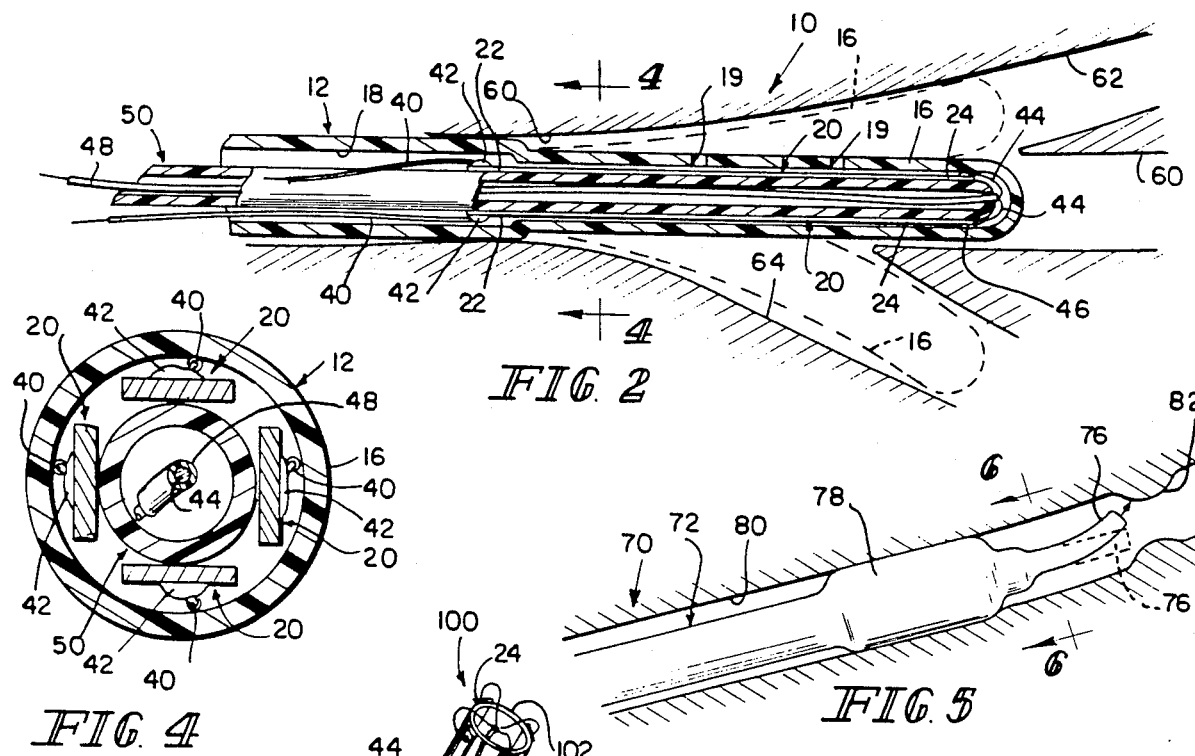
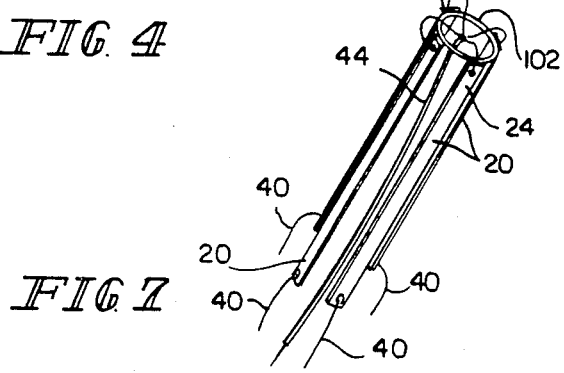
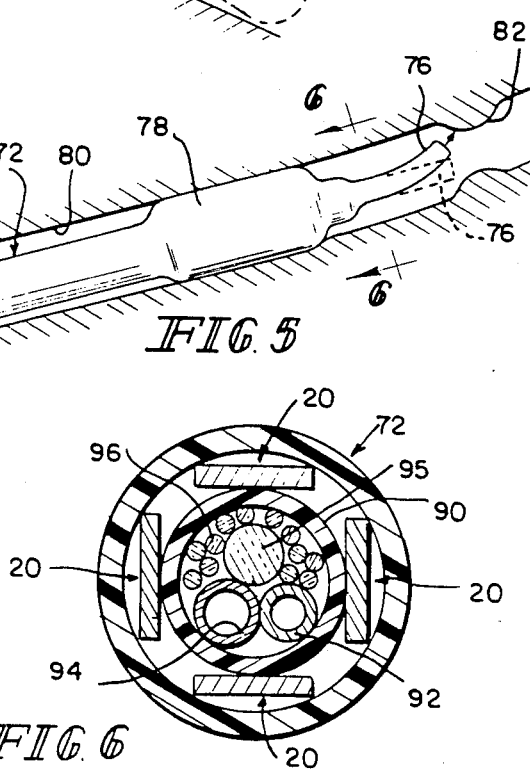

STEERABLE AND AIMABLE CATHETER

BACKGROUND AND SUMMARY OF THE INVENTION

This application is a continuation-in-part of copending application Ser. No. 06/728,634 filed May 3, 1985, now U.S. Pat. No. 4,601,705 which is a continuation-in-part of application Ser. No. 06/547,402 filed Oct. 31, 1983, now U.S. Pat. No. 4,543,090 issued Sept. 24, 1985.

The present application relates to catheters, cannulae, and the like and particularly to catheters that are steerable through body cavities and aimable at obstructions, organs, or tissue within the body from a position external to the body.

Some attempts have been made in the past to provide catheters having distal ends which, when inserted into a body, are manipulatable to advance the catheter through body cavities. See for example, U.S. Pat. Nos. 3,674,014 and 3,773,034. The catheter disclosed in U.S. Pat. No. 3,674,014 includes permanent magnets and employs a magnetic field to bend the distal end of the catheter. The catheter disclosed in U.S. Pat. No. 3,773,034 includes fluid conduits and employs a fluid to bend the distal end of the catheter. Other controlled devices are disclosed in U.S. Pat. Nos. 3,605,725 and 4,176,662. However, these prior devices are quite difficult to control and manipulate.

Some work has previously been done to produce a catheter which is readily insertable while being effectively anchorable in a body cavity. See, for example, U.S. Pat. Nos. 3,729,008 and 3,890,977.

In U.S. Pat. No. 3,890,977 to Wilson, the distal end of the catheter is formed into a desired shape by using a material exhibiting mechanical memory that is triggered by heat. By heating the mechanical memory material, the distal end of the catheter is shaped to anchor the catheter within the body. However, the change of the shape or other movement of the distal end in these prior devices is limited to a single direction. Once the memory material has been heated causing the distal end to move in said single direction to assume its characteristic anchoring shape, it becomes necessary to deform the distal end manually at a temperature below the transition temperature of the mechanical memory material in order to change the shape of the distal end. The need for manual manipulation of a catheter once it is inserted into a body limits the steerability and aimability of the catheter.

Other devices are known for guiding a catheter to a particular location within the body. See for example U.S. Pat. No. 3,043,309.

One object of the present invention is to provide a steerable catheter, cannula, and the like which is easy to operate and steerable in a plurality of different directions within the body.

Another object of the present invention is to provide an aimable catheter, cannula, and the like which is easy to operate and which can be aimed at obstructions, organs, or tissues in a plurality of different directions within the body.

Yet another object of the present invention is to provide a catheter of improved maneuverability having means for slidably coupling each of a plurality of temperature-activated memory elements to a core member so that each memory element is permitted to slip in relation to the adjacent core member when at least one of the memory elements is heated to assume a predetermined "memorized" shape.

Another object of the present invention is to provide a steerable and aimable catheter of very simple design having only one temperature-activated memory element that is movable to a predetermined shape using remote controls to steer and aim the catheter and yet is automatically returnable to an initial shape without manual manipulation by an operator.

Still another object of the present invention is to provide a highly maneuverable catheter having at least one resilient element for biasing the distal end of the catheter to assume an initial shape and a separate temperature-activated memory element that is movable under heat to bend the distal end of the catheter to a multiplicity of shapes other than the initial shape.

According to the present invention, a catheter includes an elongated tubular member having a distal end for ready insertion into a body and a temperature-activated memory element in the distal end of the tubular member. Control means is also provided for selectively heating the temperature-activated memory element. When heated to a predetermined temperature, the memory element moves in a first direction to assume a first predetermined shape, thereby deflecting the distal end of the tubular member in the first direction.

The catheter further includes return means within the distal end of the hollow tubular member for applying a force to move the memory element in a second direction away from the first direction when the temperature of the memory element is less than the predetermined temperature. Thus, the memory element is moved to assume a shape other than the first Predetermined shape and deflect the distal end of the tubular member in the second direction.

In the catheter's relaxed state, the memory element is not heated causing the distal end of the catheter to be deflected in the second direction by the return means. Thus, the catheter normally has a curved shape bending in the second direction. During steering and aiming operations, the control means is operable to heat the memory element so that it moves in the first direction to assume its first predetermined shape. The memory element exerts sufficient steering force to overcome the force applied by the return means for the purpose of deflecting the distal end of the tubular member in the first direction. Desirably, the catheter has another curved shape bending in the first direction when the memory element is heated to assume its predetermined shape. Thus, the control means is operable to straighten or bend the distal end of the catheter solely by varying the temperature of the single temperature-activated memory element.

In preferred embodiments of the present invention, the catheter includes only one temperature-activated memory element and the return means includes spring means for yieldably biasing the single temperature-activated memory element in the second direction. Such biasing causes the memory element to have a shape other than the first predetermined shape as long as the temperature of the memory element is less than the predetermined temperature. Desirably, the spring means is a resilient material preformed to define a second predetermined shape.

The return means further includes a core member within the distal end of the hollow tubular member. Each of the spring means and memory element is attached to the core member so that the spring means moves to assume a shape other than the second predetermined shape in response to movement of the memory element in the first direction.

The core member is made of a memory material and moves in the second direction to assume a second predetermined shape defined by the core member in response to cooling the memory element to a temperature that is lower than the predetermined temperature. Thus, the memory feature of the core member aids the spring means in yieldably biasing the memory element in the second direction.

A sleeve is provided for coupling both the temperature-activated memory element and spring means to a distal end of the core member so that each "bending means" (e.g. memory element or spring means) is permitted to slip in relation to the adjacent core member when at least one of the bending means moves to assume its predetermined shape. The assistive sleeve permits each bending means to slide in relation to the adjacent core member during operation of the control means. Thus, the memory element and spring means are able to slip in relation to the distal end of the core member so that maneuverability of the tubular member within the body toward a selected deflected position is increased.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a perspective view of a steerable and aimable catheter, cannula, and the like embodying the present invention;

FIG. 2 is a longitudinal cross-sectional view, partly broken away, of a body cavity and the distal end of the catheter, cannula, and the like shown in FIG. 1;

FIG. 3 is a perspective view of an embodiment of a temperature-activated memory element employed in the catheter, cannula, and the like showing its different shapes;

FIG. 4 is a transverse cross-sectional view of the distal end of the catheter, cannula, and the like embodying the present invention taken generally along section lines 4—4 in FIG. 2;

FIG. 5 is a longitudinal cross-sectional view of a body cavity showing the aimable feature of a catheter, cannula, and the like embodying the present invention;

FIG. 6 is a transverse cross-sectional view of the embodiment of the catheter, cannula, and the like shown in FIG. 5 taken generally along section lines 6—6 of FIG. 5;

FIG. 7 is a perspective view of an embodiment of a plurality of temperature-activated memory elements employed in the distal end of the catheter, cannula, and the like to deflect or move the distal end for steering and aiming thereof;

DETAILED DESCRIPTION OF THE DRAWINGS

Figure 8:
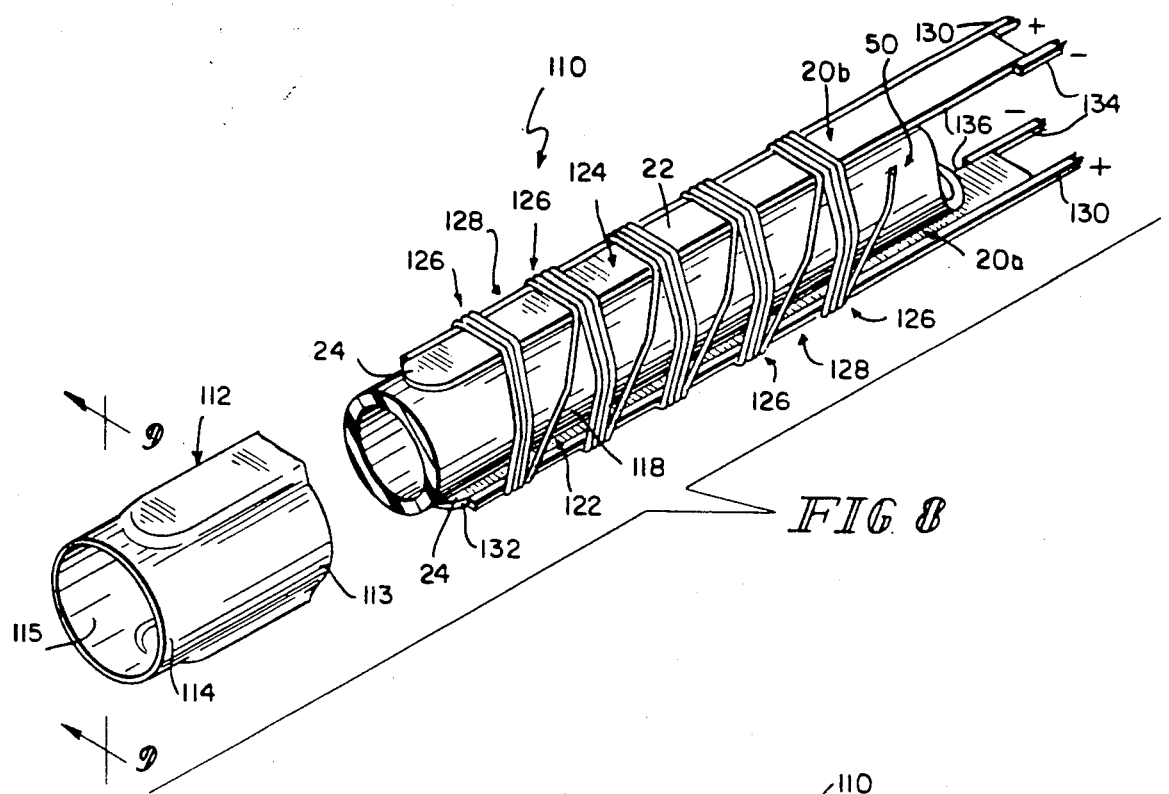
FIG. 8 is an exploded view of another embodiment of the present invention.

A catheter 10 embodying the present invention is shown generally in FIG. 1. Catheter 10 includes an elongated tubular member 12 having a proximal end 14 and a steerable and aimable distal end 16. In the illustrative embodiment, the tubular member 12 is formed of plastic, TEFLON, or cross-linked kynar or polyethylene. As will become apparent in the description of catheter 10, it is desirable that tubular member 12 be formed of a material that is flexible, that can withstand heat, and which provides electrical insulation.

As best shown in FIG. 2, the tubular member 12 can have a lumen 18 for the passage of fluid from the proximal end 14 to the distal end 16 and vice versa. Typically, the tubular member 12 includes one or more holes or openings 19 through which fluids are either injected into or drained from a body cavity. Some cannulae may have an open distal end 16 for insertion and withdrawal of medical instruments.

As shown in FIGS. 2 and 3, a plurality of temperature-activated memory elements 20 are incorporated into the distal end 16 of the tubular member 12. It may be desirable to isolate the memory elements 20 from the body cavity. The temperature-activated memory elements 20 preferably exhibit a memory characteristic in response to temperature changes. The elements 20 may be wires or flat strips such as shown in FIG. 3. In the illustrative embodiment, the temperature-activated memory elements 20 are formed of a mechanical memory metal such as a nickel titanium alloy. While a nickel titanium alloy is desirable, other metal elements having a memory characteristic related to temperature could be used without departing from the scope of the invention. Such metal elements should have a high resistance to electric current so that heat is produced when current is passed therethrough.

As shown in FIG. 3, the elements 20 have a body portion 22 and a tip portion 24. Each element 20 has a first or preset shape represented by the broken lines in FIG. 3 and a second shape represented by the solid lines in FIG. 3. Illustratively, the preset shape is an arcuate shape, and the second shape is a straight shape. It will be appreciated that the preset shape could be any shape.

Each temperature-activated memory element 20 is originally annealed into its preset shape (represented by the broken lines in FIG. 3). Memory elements 20 are cooled and straightened to their second shape (represented by the solid lines in FIG. 3) before incorporation into the distal end 16 of the tubular member 12. When the elements 20 are again heated to a predetermined transitional temperature they return to their preset shape. By applying an opposing force to an element 20 that has moved to assume its preset shape it can be moved to its second shape (represented by the solid lines in FIG. 3). In the illustrative embodiment, the predetermined transitional temperature is any temperature above body temperature. For example, the predetermined transitional temperature may be in the range of 100° to 150° F.

The memory elements 20 can either be directly incorporated into the distal end 16 of the tubular member 12 or can be carried on an electrically insulative core 50. As will be discussed later, each memory element 20 must be coupled to at least one other memory element 20 so that when one of the memory elements is heated it applies a force to move the other memory element 20.

The catheter 10 further includes an electronic control system 30 for controlling current flow to vary the temperature of each temperature-activated memory element 20 from a position external to the body so as to deflect the distal end 16 of the tubular member 12 in a plurality of different directions corresponding to the preset shapes of the elements 20. The control system 30 includes a power supply source 32 which may be either AC or DC. The system 30 also includes a control device 34 which, in the illustrative embodiment, is similar to a "joystick" control, tactile membrane switch, or ball controller. It will be appreciated that various types of control devices 34 may be employed without departing from the scope of the present invention.

The power supply source 32 is coupled through control device 34 to the tubular member 12 by cable 36 and a coupling device 38. Further, the temperature-activated memory elements 20 are electrically connected to the control device 34 through cable 36 and coupling 38 by electrical wires 40 which are attached to the body portions 22 of memory elements 20 by conventional means 42 such as soldering or crimping. Return or ground wires 44 are attached to the tip portions 24 of memory elements 20 by conventional means such as soldering or crimping 46. Return or ground wires 44 may be combined into a single ground cable 48 as shown in FIG. 2.

In the embodiment illustrated in FIG. 2, the temperature-activated memory elements 20 are carried on the exterior of the core 50 and ground wire 48 runs through the interior of the core 50. Core 50 couples each memory element 20 to at least one other memory element 20 so that when a memory element 20 moves to assume its preset shape in response to heat it applies a force to move the other memory element 20 coupled thereto. In preferred embodiments, the core 50 is a tube formed of urethane having a wall thickness of about 0.005 inch. In other embodiments, the core 50 may be a fiber optics bundle, electrical wire, micro-instrumentation, or any other suitable member. Other mounting arrangements could be used for incorporating the memory elements 20 into the distal end 16 of the tubular member 12 without departing from the scope of the present invention.

In operation, the distal end 16 of the tubular member 12 is inserted into a body cavity 60 such as a blood vessel while memory elements 20 are straight and at a temperature below the transitional temperature. At this stage, each memory element 20 is in its second shape for ready insertion of the distal end 16 into the body cavity 60. The tubular member 12 is pushed through cavity 60 until it reaches a desired branch 62 or 64 extending from the cavity 60. Control device 34 is manipulated to apply an electrical voltage or current to one or more of the memory elements 20. Because of the high resistance of memory elements 20, heat is generated. When a memory element is heated to its predetermined transitional temperature (i.e., a predetermined temperature above body temperature) the memory element 20 moves to assume its preset shape (as shown by the broken lines in FIG. 3), thereby deflecting or moving the distal end 16 of tubular member 12 into one of the desired branch cavities 62 or 64. Once the distal end 16 is in the branch 62 or 64, power can be removed from the memory element 20 to allow it to cool. While the memory element 20 is at a temperature above its predetermined transitional temperature it remains relatively stiff in its preset shape. When the memory element 20 cools to a temperature below its predetermined transitional temperature it becomes soft or pliable in its preset shape. After cooling, a voltage or current is applied to another memory element 20 coupled to the cooled memory element 20 still in its preset shape. When the other memory element 20 reaches its predetermined transitional temperature, it begins to move to assume its preset shape and in doing so applies a force to the memory element 20 coupled thereto to move it to its second shape (as shown by the solid lines in FIG. 3). The catheter tubular member 12 can continue to be pushed through the branch 62 or 64 until it is again desirable to turn or bend the catheter 10.

As illustrated in FIG. 4, four temperature-activated memory elements 20 may be carried on the exterior of core 50. In the illustrative embodiment, pairs of the memory elements 20 are shown diametrically opposed to each other so that opposed elements 20 apply forces to each other when they are heated. Thus, the distal end 16 may be deflected in at least four different directions by applying an electrical current or voltage to one of the memory elements 20. It will be appreciated that more or less than four memory elements 20 may be utilized without departing from the scope of the present invention. However, it should be noted that at least two memory elements 20 are required. Further, it may be desirable to apply an electrical voltage or current to more than one of the memory elements 20 simultaneously to increase the number of directions in which the distal end 16 of the tubular member 12 may be deflected. The control system 30 may include means for regulating the application of current or voltage applied to the memory elements 20 to allow virtually an unlimited number of directions in which the distal end 16 may be deflected for the purpose of steering the catheter tubular member 10 through body cavities. It will be appreciated that a large number of wire memory elements could be incorporated into the distal end 16 and a voltage or current applied to one or more of the wires to deflect the distal end 16 in a desired direction.

Another application for a catheter 70 embodying the present invention is shown in FIGS. 5 and 6. Reference numerals from FIGS. 1–4 have been applied to the catheter 70 shown in FIGS. 5 and 6 where the same or similar parts are being used. Catheter 70 includes a tubular member 72 having a distal end 76. The distal end 76 includes a plurality of temperature-activated memory elements 20 of the type previously described. The same or similar control system may be employed in connection with the catheter 70 in a body cavity 80 for the purpose of aiming the distal end 76 at an obstruction, organ, or tissue 82 within the cavity 80. The catheter 70 may be anchored in the cavity 80 by a balloon 78. Once the catheter 70 is anchored, the distal end 76 is aimed in one of a plurality of directions to establish a course for the injection of fluid or a laser beam at the organ or tissue 82.

As shown in FIG. 6, a core 90 formed of insulative material passes through tubular member 72. Memory elements 20 are carried on the core 90 between the core 90 and the tubular member 72. Core 90 serves to couple each memory element 20 to at least one other memory element 20 in the manner and for the purpose previously described. The hollow core 90 may include a first tube 92 for carrying a fluid from the proximal end of the catheter 70 to the distal end 76. A return tube 94 may be included for extracting fluid. It will be appreciated that either passage 92 or 94 may be used for inserting a medical instrument into the cavity 80. Core 90 may also include a transparent member 95 providing a lens for observing the obstruction, organ, or tissue 82 and a bundle of fiber-optic lines 96 for transmitting light or a laser beam to the distal end 76. Thus, in the embodiment illustrated in FIGS. 5 and 6, catheter 70 has a distal end 76 which is aimable in a plurality of directions in accordance with the present invention for the purpose of establishing a course for the injection of fluid, light, or a laser beam at an obstruction, organ, or tissue 82.

Another embodiment of an arrangement for the memory elements 20 is shown in FIG. 7. The memory element arrangement 100 includes a plurality of memory elements 20 coupled at their distal ends 24 by a thermally and electrically insulative ring 102. Various materials, such as plastic, may be used to construct the ring 102. Ground wires from each memory element 20 are channeled through a common ground wire conduit 44. Ring 102 serves to couple the memory elements 20 to each other and performs a function similar to cores 50 and 90. This arrangement facilitates the mounting of the memory elements 20 in the distal end 16, 76 of the catheters 10, 70, respectively.

Yet another embodiment of the present invention is shown in FIGS. 8-11. Reference numerals from FIGS. 1-4 have been applied to a catheter 110 shown in FIGS. 8-11 where the same or similar parts are being used. Catheter 110 includes a tubular member 12, a pair of temperature-activated memory elements 20a and 20b, and a core 50 of the types described above. Memory elements 20a and 20b may be flat as shown in FIGS. 8-11 or in some applications may be wires, particularly where more than two memory elements are employed. The catheter 110 further includes a sleeve 112 for slidably coupling each memory element 20a,b to the core member 50 so that each memory element 20a,b is permitted to slip in relation to the adjacent core member 50 when at least one of the memory elements 20a,b moves to assume its predetermined shape. The sleeve 112 also interconnects one memory element to another memory element so that when one memory element moves in a first direction to assume its preset shape a force is applied to move the other memory element in the first direction and vice-versa.

Desirably, the sleeve 112 is a resilient tubular jacket for embracing elastically the core member 50 and the memory elements 20a,b to provide a slip interface therebetween. The sleeve 112 includes an axially inner portion 113 for the reception of a distal end of the core 50 and the tip portions 24 of each memory element and an axially outer portion 114 for the reception of a forward tip portion of the core. Thus, each memory element received within the sleeve 112 simultaneously is retainable in a core-guiding position as shown in FIGS. 9-11 and is movable with the sleeve 112 to deflect the distal end of the core 50 to a selected position (e.g. the deflected position illustrated in FIG. 11).

The sleeve 112 includes an inner wall 115 defining a slip chamber 116 in which each memory element is able to slip in relation to the core member 50 during selective heating of at least one of the memory elements 20. In preferred embodiments, the sleeve 112 is formed of thin MYLAR material having a thickness of about 0.001 inch. Any other similar material that has a low coefficient of friction and is not generally susceptible to deformation under heat would be suitable.

Figure 9:
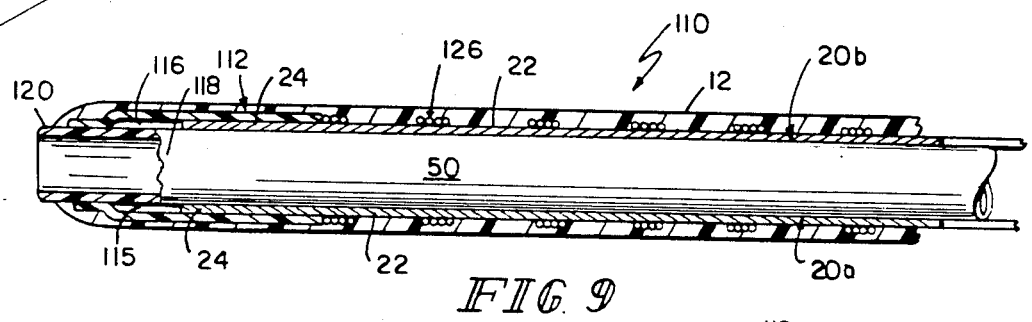
FIG. 9 is a longitudinal sectional view, partly broken away, showing the embodiment of FIG. 8 in its relaxed position and taken generally along section lines 9—9 of FIG. 8.

As shown best in FIGS. 8 and 9, the core 50 includes a distal end 118 having a forward tip portion 120. Installation of the sleeve 112 operates to position the forward tip portion 24 of each memory element 20a,b in close proximity to the distal end 118 of the core 50. The first and second memory elements 20a,b are positioned on opposite sides of the core 50 in spaced relation as shown in FIGS. 8, 9, and 11 so that the core 50 is intermediate the two memory elements. Thus, the forward tip portion 24 of each memory element is retained in its core-guiding position by sleeve 112. In addition, the remaining body portion 22 of each memory element is retained in its core-guiding position by means of a wrap.

Figure 10:
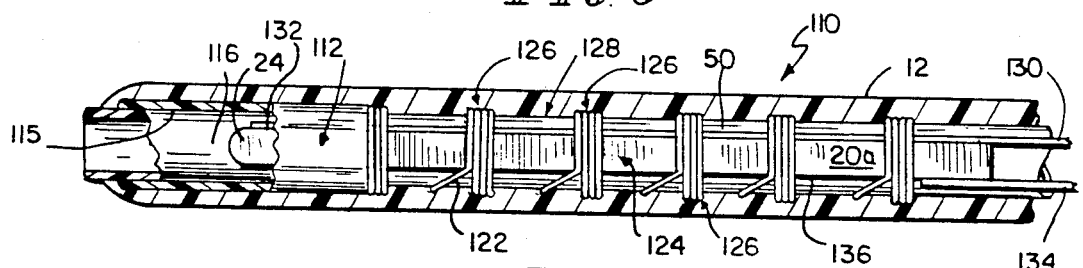
FIG. 10 is a view, partly broken away, of the embodiment of FIG. 9 rotated 90° about its longitudinal axis.
Figure 11:
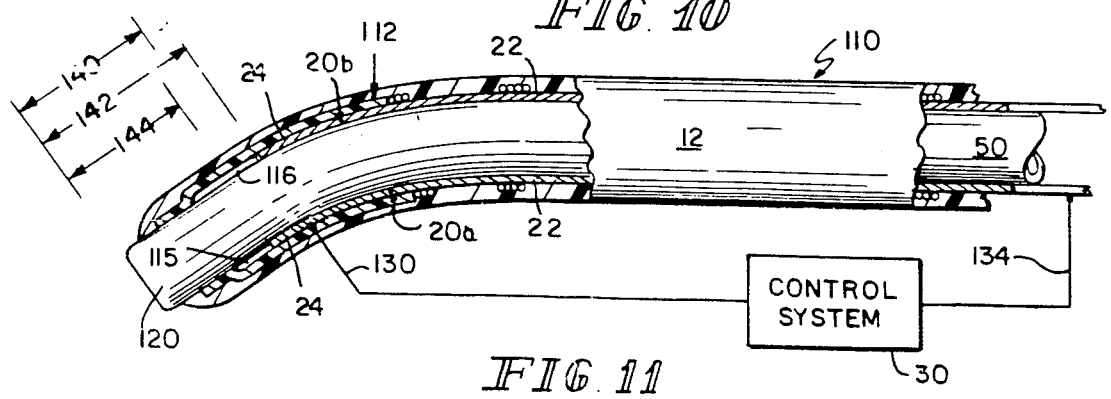
FIG. 11 is a longitudinal sectional view, partly broken away, showing the embodiment of FIG. 8 in a deflected position.

The memory element retaining wrap is desirably a continuous filament 122 as illustrated in FIGS. 8-11. For example, a nylon filament having a 0.002 inch diameter would be satisfactory. The filament wrap 122 couples at least a segment of the body portion 22 of each memory element 20a,b to the core 50 so that the body remaining portion segment is permitted to slip in relation to the adjacent core 50 when at least one of the memory elements 20a,b moves to assume its preset shape. Desirably, the filament wrap 122 embraces a radially outwardly-facing surface 124 of each of the memory elements in sufficiently tight relation to retain the memory elements in their coupled position while permitting relative slipping movement between each coupled memory element and the core 50. As shown in FIGS. 8 and 10, the continuous filament 122 defines a plurality of winding bunches 126 disposed along the length of the core 50 in spaced-apart relation so that each winding in a winding bunch 126 can move along the core in relation to one another in the spaces 128 therebetween during deflection or bending of the distal end 16 of the tubular member 12. Illustratively, each spaced winding bunch 126 includes three windings as shown in FIGS. 8 and 10.

In the embodiment illustrated in FIGS. 8-11, the temperature-activated memory elements 20a,b are electrically connected to the control device 34 by wire 130 of rectangular cross-section. The remainder of rectangular wire 130 is mounted along the side edge 132 of the remaining portion 22 of each memory element 20. Return or ground wire 134 is also of rectangular cross-section and mounted along another side edge 136 of each memory element at a proximal end of the remaining body portion 22 of the memory element. Other suitable electrical coupling means are usable to couple the memory elements of the embodiment of FIGS. 8-11 to the control device 34 without departing from the scope of the present invention.

In operation, the sleeve 112 included in the embodiment of FIGS. 8-11 provides numerous advantages. One advantage is that maneuverability of the catheter 110 is improved due to slippage of each memory element 20a,b relative to core 50 in the slip chamber 116 defined by the sleeve 112. A certain amount of slippage is desirable to allow relative movement of the memory elements 20 and the core 50 to improve the flexibility of the catheter. As shown best in FIG. 11, movement of the first memory element 20a to assume its predetermined position causes the forward tip portion 24 of the first memory element 20a to move along the exterior surface of the core 50 toward the forward tip portion 120 of the core 50 and the forward tip portion 24 of the second memory element 20b to move along the exterior surface of the core 50 away from the forward tip portion 120 of the core 50. In other words, the first memory element 20b is arcuately shaped when the memory element 20a moves to assume its predetermined shape and vice versa. In particular, the arc defined by the memory element 20a is smaller than the arc defined by the equidistantly spaced-apart memory element 20b as shown in FIG. 11. The slippage of memory elements 20a and 20b relative to the forward tip portion 120 of core 50 is shown by the arrows in FIG. 11. Arrow 140 represents the positions of the tips 24 before deflection and arrows 142 and 144 represent the positions of the tips 24 of elements 20b and 20a respectively when the catheter is deflected.

Figure 12:
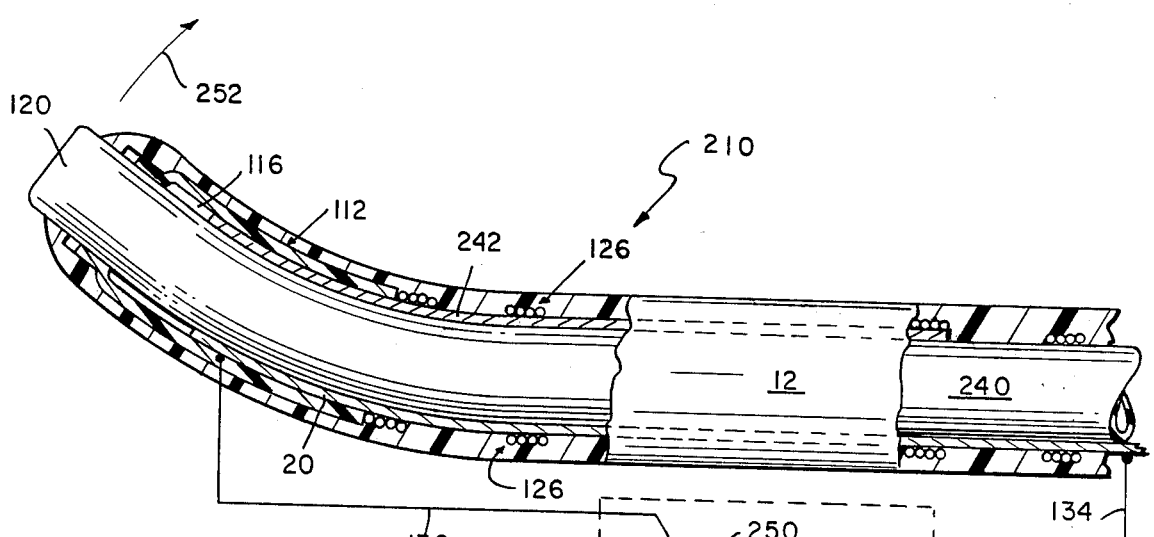
FIG. 12 is a longitudinal sectional view of yet another embodiment of the present invention, partly broken away, showing the distal end of a catheter in a relaxed position.
Figure 13:
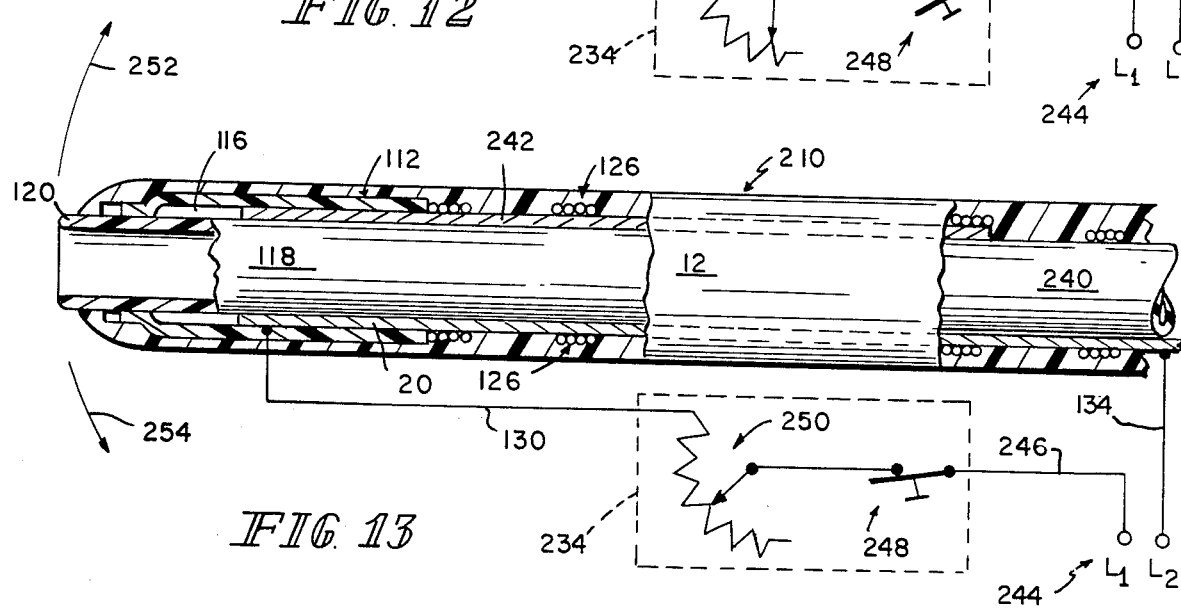
FIG. 13 is a view of the embodiment of FIG. 12, partly broken away, showing the distal end of the catheter in a partially deflected position.
Figure 14:
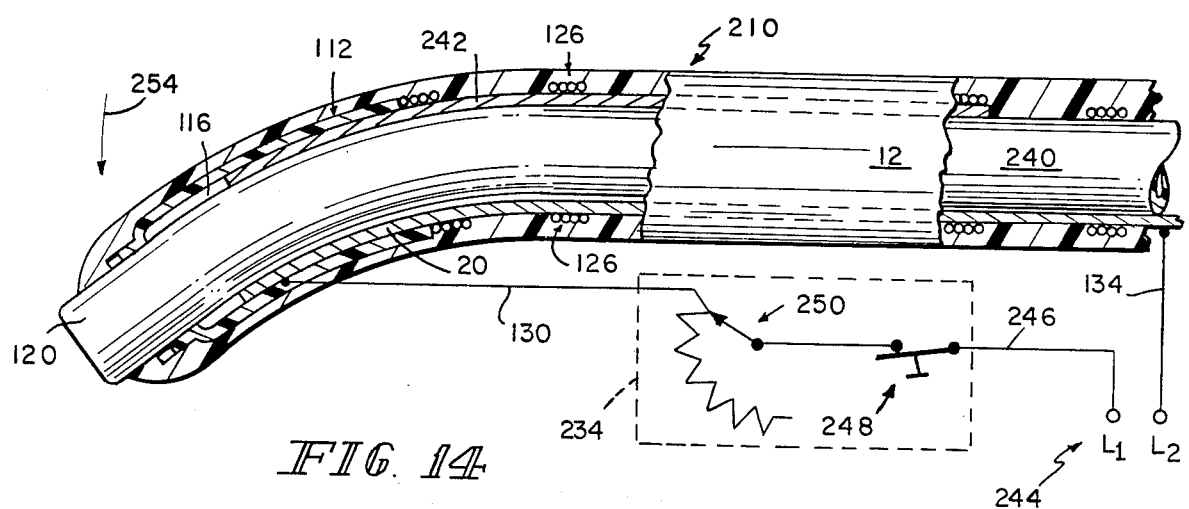
FIG. 14 is a view of the embodiment of FIG. 12, partly broken away, showing the distal end of the catheter in a fully deflected position.

Still another embodiment of the present invention is shown in FIGS. 12-14. Reference numerals from FIGS. 1-4 and 8-11 have been applied to a catheter 210 as shown in FIGS. 12-14 where the same or similar parts are being used. Catheter 210 includes a tubular member 12, a temperature-activated memory element 20, and a sleeve 112 of the types described above.

An electrically insulative hollow core member 240 is provided in the interior of tubular member 12 for receiving medical instruments, fiber optics lines, fluid-conducting tubes, or other medical or optical tools. Core member 240 is desirably made of plastics material such as urethane, TEFLON, KYNAR, or polyethylene and has a wall thickness of 0.005-0.010 inch (1.27-2.54 mm). In contrast to the core members illustrated in connection with the embodiments of FIGS. 1-11 that are generally straight in their relaxed positions, core member 240 is preformed using known techniques to assume a curved shape in its relaxed position as shown in FIG. 12.

The catheter 210 further includes a spring 242 positioned on the exterior of curved core member 240 in diametrically opposed relation to memory element 20. The spring 242 is desirably made of stainless steel or plastics material and has a thickness of 0.010 inch (2.54 mm). The spring 242 is also preformed using known techniques to assume a curved shape. As shown in FIG. 12, the radius of curvature of preformed spring 242 is less than the radius of curvature of curved core member 240.

Spring 242 effectively serves as a resilient memory element and cooperates with core 240 to load memory element 20 with a force that bends memory element 20 to an initial shape illustrated in FIG. 12. The spring constant of spring 242 is selected to cause spring 242 to bend the distal end of the catheter in one direction as shown in FIG. 12 and also yield under loading provided by the heated memory element 20 to permit the distal end of the catheter to bend in an opposite second direction as shown in FIGS. 13 and 14.

Sleeve 112 slidably couples memory element 20 and preformed spring 242 to curved core member 240 so that the memory element 20 and spring 242 are permitted to slip in relation to the adjacent core member 240 when either of the memory element 20 and the spring 242 move to assume its preset shape. The sleeve 112 also interconnects memory element 20 to spring 242 so that when the memory element 20 moves in a first direction 254 to assume its preset shape a force is applied to move the spring 242 in the first direction 254 and vice versa.

In the diagrammatic embodiment illustrated in FIGS. 12-14, the temperature-activated memory element 20 is electrically connected to a control device 234 and a power supply 244 by wires 130, 134, and 246. Control device 234 includes switch means 248 and power control means 250. Switch means 248 is operable to decouple the power supply 244 and the memory element 20 to prevent heating of memory element 20. Power control means 250 is operable to vary the electrical power provided to memory element 20, thereby regulating the amount of heat applied to memory element 20. Illustratively, power control means 250 is a rheostat. It will be appreciated by those skilled in the art that the manner of controlling the temperature of memory element 20 can be accomplished using a variety of control systems other than the illustrated system without departing from the scope of the present invention.

One exemplary operation sequence of catheter 210 is illustrated in FIGS. 12-14. In particular, the relaxed state of the distal end of tubular member 12 is shown in FIG. 12. The preset curved shapes of core member 240 and spring 242 act to bend the distal end of tubular member 12 in direction 252 as shown in FIG. 12. At this stage, switch means 248 is in its open circuit position, preventing current generated by power supply 244 from being applied to heat the memory element 20. Thus, the relatively cool memory element 20 is also bent in direction 252 due to the interconnection with core member 240 and spring 242 established by sleeve 112 and tubular member 12. Such bending resulting from the preset curved shapes of core member 240 and spring 242 effectively defines an "initial position" of the memory element 20 and the distal end tubular member 12.

Steering and aiming of catheter 210 is accomplished by operation of control device 234 in the following manner. Once switch means 248 is moved to its closed circuit position shown in FIGS. 13 and 14, the operator can control the heating and cooling of the temperature-activated memory element 20 by using power control means 250.

Movement of power control means 250 to a first setting illustratively depicted in FIG. 13 causes a sufficient amount of power to be applied to memory element 20 so that the memory element 20 is heated and moves in direction 254 away from its initial curved shape to assume a substantially straight shape. The steering force generated by such movement is transmitted to core member 240 and spring 242 in part via sleeve 112. This steering force is sufficient to overcome opposing "return" forces generated by core member 240 and spring 242.

Continued movement of power control means 250 to another power setting illustratively depicted in FIG. 14 causes still more power to be applied to memory element 20. This heats memory element 20 to a higher "predetermined" temperature, causing the memory element 20 to continue to move in direction 254 to assume a "predetermined" curved shape.

Return of the catheter 210 to its initial relaxed state shown in FIG. 12 is easily accomplished by using control device 234 to lessen the amount of power applied to memory element 20. This step allows memory element 20 to cool, thereby permitting preset core member 240 and spring 242 to cooperate to exert a return force on the distal end of the tubular member 12 and memory element 20. Such a return force acts in direction 252 in the absence of a steering force generated by memory element 20, thereby causing catheter 210 to be returned to its relaxed state.

It will be appreciated that a plurality of pairs of temperature-activated memory elements 20 and springs 242 could be positioned in the distal end of the catheter to provide a great deal of flexibility in steering and airming the catheter. However, it will be understood that it is possible to steer and aim a catheter provided with only a single temperature-activated memory element 20 and return spring 242 in a multiplicity of radial directions by rotating the catheter about its central longitudinal axis during heating of memory element 20 using control device 234.

While illustrative embodiments and uses of catheters, cannulae, and the like embodying the present invention have been shown and described, it will be appreciated that various modifications may be made to the illustrative embodiments without departing from the scope of the present invention.

What is claimed is:

1. An apparatus comprising
    an elongated tubular member having a proximal end and a distal end for insertion into the body,
    a temperature-activated memory element in the distal end of the tubular member, the memory element moving in a first direction to assume a first predetermined shape and deflect the distal end of the tubular member in the first direction when heated to a predetermined temperature,
    resilient means within the distal end of the tubular member providing a predetermined bias for applying a force to move the distal end of the tubular member in a second direction away from the first direction to assume a predetermined curved shape when the temperature of the memory element is less than the predetermined temperature so that the memory element is moved to assume a shape other than the first predetermined shape in response to movement of the distal end of the tubular member to assume the predetermined curved shape, the resilient means being coupled to the temperature-activated memory element so that when the memory element moves in the first direction to assume its first predetermined shape a force is applied to move the resilient means in the first direction and when the resilient means moves in the second direction upon cooling of the memory element to a temperature less than the predetermined temperature a force is applied to move the memory element in the second direction, and
    control means for selectively heating the memory element so that the memory element is moved in the first direction to overcome the force applied by the resilient means and deflect the distal end of the tubular member in the first direction so that the distal end of the tubular member is moved to assume a selected shape other than its predetermined curved shape.

2. The apparatus of claim 1, wherein the control means includes a power supply source, means for coupling the power supply source to the memory element, and a control device for steering the distal end of the tubular member through cavities of the body, the control device including means for selectively varying the power applied to heat the memory element and means for selectively disabling the coupling means to decouple the power supply source and the memory element so that the resilient means acts to move the distal end of the tubular member in the second direction away from the first direction to assume the predetermined curved shape causing the memory element to move to assume a shape other than the first predetermined shape.

3. The apparatus of claim 1, wherein the resilient means includes spring means for yieldably biasing the memory element in the second direction and the spring means has a predetermined spring constant causing the spring means to apply a primary return force of a magnitude sufficient to move the memory element to assume a shape other than the first predetermined shape while the temperature of the memory element is less than the predetermined temperature.

4. The apparatus of claim 3, wherein the memory element and the spring means are located in diameterically opposed relationship to each other in the distal end of the tubular member.

5. The apparatus of claim 3, wherein the spring means is made of a resilient material preformed to define a second predetermined shape and the spring means moves to assume a shape other than the second predetermined shape in response to movement of the memory element in the first direction.

6. The apparatus of claim 5, wherein the resilient means further includes interconnecting means for connecting the memory element to the spring means, the interconnecting means transmits a steering force from the memory element to the spring means to overcome the opposing return force generated by the spring means, thereby moving the spring means in the first direction in response to movement of the memory element in the first direction to assume the first predetermined shape during exposure to heating temperature, and the interconnecting means transimits the return force generated by the spring means to the memory element to move the memory element in the second direction in response to movement of the spring means in the second direction to assume the second predetermined shape during exposure to cooliing temperature.

7. The apparatus of claim 6, wherein the interconnecting means is a core member made of a resilient material and preformed to assume a curved shape.

8. An apparatus comprising
    an elongated tubular member having a proximal end and a distal end for insertion into the body,
    a temperature-activated memory element in the distal end of the tubular member, the memory element moving in a first direction to assume a first predetermined shape and deflect the distal end of the tubular member in the first direction when heated to a predetermined temperature,
    resilient means within the distal end of the tubular member having a predetermined bias for applying a force to move the memory element in a second direction away from the first direction when the temperature of the memory element is less than the predetermined temperature so that the memory element is moved to assume a shape other than the first predetermined shape and deflect the distal end of the tubular member in the second direction, and
    control means for selectively heating the memory element so that the memory element is moved in the first direction to overcore the force applied by the resilient means and deflect the distal end of the tubular member in the first direction, the resilient means further including a core member within the distal end of the tubular member, and each of the spring means and memory element is attached to the core member.

9. The apparatus of claim 8, wherein the core member and the tubular member are interconnected so that guided movement of the core member in response to operation of at least one of the memory element and the spring means moves the tubular member to a selected deflected position.

10. The apparatus of claim 8, wherein the core member is made of a resilient material preformed to define a second predetermined shape and the core member moves to assume a shape other than the second predetermined shape in response to movement of the memory element in the first direction.

11. The apparatus of claim 8, wherein the core member is made of a memory material having a predetermined spring constant and the core member applies an auxiliary return force of a magnitude sufficient to aid the spring means in yieldably biasing the temperature-activated memory element in the second direction while the temperature of the memory element is less than the predetermined temperature.

12. An apparatus comprising
an elongated tubular member having a proximal end and a distal end for insertion into the body,
a temperature-activated memory element in the distal end of the tubular member, the memory element moving in a first direction to assume a first predetermined shape and deflect the distal end of the tubular member in the first direction when heated to a predetermined temperature,
resilient means within the distal end of the tubular member having a predetermined bias for applying a force to move the memory element in a second direction away from the first direction when the temperature of the memory element is less than the predetermined temperature so that the memory element is moved to assume a shape other than the first predetermined shape and deflect the distal end of the tubular member in the second direction, and
control means for selectively heating the memory element so that the memory element is moved in the first direction to overcome the force applied by the resilient means and deflect the distal end of the tubular member in the first direction, the resilient means including spring means for yieldably biasing the memory element in the second direction and the spring means having a predetermined spring constant causing the spring means to apply a primary return force of a magnitude sufficient to move the memory element to assume a shape other than the first predetermined shape while the temperature of the memory element is less than the predetermined temperature, the resilient means further including a core member within the distal end of the hollow tubular member and sleeve means for slidably coupling the memory element and the spring means to the core member so that each of the memory element and spring means is permitted to slip in relation to the adjacent core member during movement of the memory element to assume the first predetermined shape.

13. The apparatus of claim 12, wherein the sleeve means is a resilient tubular jacket for embracing the core member and the memory element, the tubular jacket having an inner wall defining a slip chamber in which each of the memory element and spring means is able to slip in relation to the core member during selective heating and cooling of the memory element.

14. An apparatus comprising
an elongated tubular member having a proximal end and a distal end for insertion into the body,
a temperature-activated memory element in the distal end of the tubular member, the memory element having an initial curved shape and moving to assume a predetermined shape when heated to a predetermined temperature,
control means for selectively heating the memory element to the predetermined temperature so that the memory element is moved in a first direction to deflect the distal end of the tubular member, and
spring means for yieldably urging the memory element in an opposite second direction to establish said initial curved shape and to aid in returning the memory element to its initial curved shape when the temperature of the memory element is less than the predetermined temperature, the spring means being coupled to the memory element so that when the memory element moves in the first direction to assume its predetermined shape a force is applied to move the spring means in the first direction and when the spring means moves in the second direction upon cooling of the memory element to a temperature less than the predetermined temperature a force is applied to move the memory element in the second direction.

15. The apparatus of claim 14, wherein the spring means includes a resilient member preformed to define a second predetermined shape and the resilient member moves to assure a shape other than the second predetermined shape in response to movement of the memory element in the first direction.

16. The apparatus of claim 15, wherein the spring means further includes interconnecting means for connecting the memory element to the resilient member, the interconnecting means transmits a steering force from the memory element to the resilient member to move the resilient member in the first direction and overcome an opposing return force generated by the resilient member in response to movement of the memory element in the first direction to assume the first predetermined shape during exposure to heating temperature, and the interconnecting means transmits a return force generated by the resilient member to the memory element to move the memory element in the second direction in response to movement of the resilient member in the second direction to assume the second predetermined shape during exposure to cooling temperature.

17. An apparatus comprising
an elongated tubular member having a proximal end and a distal end for insertion into the body,
a temperature-activated memory element in the distal end of the tubular member, the memory element having an initial shape and moving to assume a predetermined shape when heated to a predetermined temperature,
a control means for selectively heating the memory element to the predetermined temperature so that the memory element is moved in a first direction to deflect the distal end of the tubular member, and spring means for yieldably urging the memory element in an opposing second direction to establish said initial shape and to aid in returning the memory element to its initial shape when the temperature of the memory element is less than the predetermined temperature, the spring means being coupled to the memory elemet so that when the memory element moves in the first direction to asume its predetermined shape a force is applied to move the spring means in the first direction and when the spring means moves in the second direction upon cooling of the memory element to a temperature less than the predetermined temperature a force is applied to move the memory element in the second direction, the spring means including a core member within the distal end of the tubular member, the core member being made of a resilient material preformed to define a second predetermined shape, and the core member moving to assume a shape other than the second predetermined shape in response to movement of the memory element in the first direction.

18. An apparatus comprising
an elongated tubular member having a proximal end and a distal end for insertion into the body,
a temperature-activated memory element in the distal end of the tubular member, the memory element having an initial shape and moving to assume a predetermined shape when heated to a predetermined temperature,
control means for selectively heating the memory element to the predetermined temperature so that the memory element is moved in a first direction to deflect the distal end of the tubular member, and
spring means for yieldably urging the memory element in an opposing second direction to establish said initial shape and to aid in returning the memory element to its initial shape when the temperature of the memory element is less than the predetermined temperature, the spring means being coupled to the memory element so that when the memory element moves in the first direction to assume its predetermined shape a force is applied to move the spring means in the first direction and when the spring means moves in the second direction upon cooling of the memory element to a temperature less than the predetermined temperature a force is applied to mvoe the memory element in the second direction, the proximal end of the elongated tubular member including a central axis, the initial shape established substantially by the spring means being a curved shape bending away from the central axis in the second direction to deflect the distal end of the tubular member in the second direction, and the predetermined shape being another curved shape bending away from the central axis in the first direction to deflect the distal end of the tubular member in the first direction.

19. The apparatus of claim 18, wherein the memory element has a first radius of curvature and the spring means is a resilient member having a second radius of curvature that is less than the first radius of curvature when the memory element moves to assume its initial shape and greater than the first radius of curvature when the memory element moves to assume its predetermined shape.

20. An apparatus comprising
an elongated tubular member having a proximal end and a distal end for insertion into the body,
a core member within the distal end of the hollow tubular member,
first and second memory elements in the distal end of the hollow tubular member, the first memory element being made of a temperature-activated memory material and moving to assume a first predetermined shape and deflect the distal end of the tubular member in one direction when heated to a predetermined temperature, the second memory element being made of a resilient memory material and moving to assume a second predetermined shape and deflect the distal end of the tubular member in another direction when the temperature of the first memory element is less than the predetermined temperature,
sleeve means for slidably coupling each memory element to the core member so that each memory element is permitted to slip in relation to the adjacent core member when at least one of the memory elements moves to assume its predetermined shape, and
control means for selectively heating the first memory element to move the first memory element to assume the first. predetermined shape, thereby exerting a force on the core member sufficient to overcome force exerted on the core member by the second memory element and causing the second memory element to move to assume a shape other than the second predetermined shape, the core member being made of a resilient material preformed to define a third predetermined shape and the core member moving to assume a shape other than the third predetermined shape in response to movement of the first memory element to assume the first predetermined shape.

21. The apparatus of claim 20, wherein the first, second, and third predetermined shapes are curved shapes.

22. The apparatus of claim 21, wherein the radius of curvature of the third predetermined shape is greater than the radius of curvature of the second predetermined shape.

23. An apparatus comprising
an elongated tubular member having a proximal end and a distal end for insertion into the body,
a core member within the distal end of the hollow tubular member,
first and second memory element in the distal end of the hollow tubular member, the first memory element being made of a temperature-activated memory material and moving to assume a first predetermined shape and deflect the distal end of the tubular member in one direction when heated to a predetermined temperature, the second memory element being made of a resilient memory material and moving to assume a second predetermined shape and deflect the distal end of the tubular member in another direction when the temperature of the first memory element is less than the predetermined temperature,
sleeve means for slidably coupling each memory element to the core member so that each memory element is permitted to slip in relation to the adjacent core member when at least one of the memory elements moves to assume its predetermined shape, and control means for selectively heating the first memory element to move the first memory element to assume the first predetermined shape, thereby exerting a force on the core member sufficient to overcome force exerted on the core member by the second memory element and causing the second memory element to move to assume a shape other than the second predetermined shape, the distal end of the tubular member being formed of flexible non-conductive material and the first memory element being formed of a metal having a relatively high electrical resistance.

24. The apparatus of claim 23, wherein the tubular member includes means for providing a passageway therethrough and the first and second memory elements are disposed exterior to the passageway in the distal end of the tubular member.

25. The apparatus of claim 24, wherein the tubular member further includes light-transmitting means in the passageway for transmitting light from the proximal end to the distal end of the tubular member.

26. The apparatus of claim 25, wherein the control means includes a power supply source, means for coupling the power supply source to the first memory element, and a control device for selectively applying power to heat the first memory element to aim the distal end and light-transmitting means to the tubular member at a desired object in the body.

27. The apparatus of claim 26, wherein the first memory element is formed of a nickel titanium alloy.

28. The apparatus of claim 27, wherein the tubular member further includes fluid-transmitting means in the passageway for transmitting fluid from the proximal end to the distal end of the tubular member and vice versa.

29. An apparatus comprising
an elongated tubular member having a proximal end and a distal end for insertion into the body,
a core member within the distal end of the hollow tubular member,
first and second memory elements in the distal end of the hollow tubular member, the first memory element being made of a temperature-activated memory material and moving to assume a first predetermined shape and deflect the distal end of the tubular member in one direction when heated to a predetermined temperature, the second memory element being made of a resilient memory material and moving to assume a second predetermined shape and deflect the distal end of the tubular member in another direction when the temperature of the first memory element is less than the predetermined temperature,
sleeve means for slidably coupling each memory element to the core member so that each memory element is permitted to slip in relation to the adjacent core member when at least one of the memory elements moves to assume its predetermined shape, and control means for selectively heating the first memory element to move the first memory element to assume the first predetermined shape, thereby exerting a force on the core member sufficient to overcome force exerted on the core member by the second memory element and causing the second memory element to move to assume a shape other than the second predetermined shape, the control means including a power supply source, means for coupling the power supply source to the first memory element, and a control device for selectively applying power to heat the first memory element to steer the distal end of the tubular member through cavities in the body.

30. An apparatus comprising
an elongated tubular member having a proximal end and a distal end for insertion into the body,
a core member within the distal end of the hollow tubular member,
first and second memory elements in the distal end of the hollow tubular member, the first memory element being made of a temperature-activated memory material and moving to assume a first predetermined shape and deflect the distal end of the tubular member in one direction when heated to a predetermined temperature, the second memory element being made of a resilient memory material and moving to assume a second predetermined shape and deflect the distal end of the tubular member in another direction when the temperature of the first memory element is less than the predetermined temperature,
sleeve means for slidably coupling each memory element to the core member so that each memory element is permitted to slip in relation to the adjacent core member when at least one of the memory elements moves to assume its predetermined shape, and
control means for selectively heating the first memory element to move the first memory element to assume the first predetermined shape, thereby exerting a force on the core member sufficient to overcome force exerted on the core member by the second memory element and causing the second memory element to move to assume a shape other than the second predetermined shape, the two memory elements being located in diametrically opposed relationship to each other in the distal end of the tubular member.

* * * * *

UNITED STATES PATENT AND TRADEMARK OFFICE
CERTIFICATE OF CORRECTION

PATENT NO. : 4,758,222

DATED : July 19, 1988

INVENTOR(S) : William C. McCoy

It is certified that error appears in the above-identified patent and that said Letters Patent is hereby corrected as shown below: Title page:

On the bibliography page, at [56] References Cited, please delete "3,297,008" and insert therefor --3,729,008--;

At column 2, line 33, please delete "Predetermined" and insert therefor --predetermined--;

At column 12, line 39, please delete "transimits" and insert therefor --transmits--;

At column 14, line 37, please delete "assure" and insert therefor --assume--;

At column 15, line 7, please delete "elemet" and insert therefor --element--; and At column 15, line 49, please delete "mvoe" and insert therefor --move--.

Signed and Sealed this

Tenth Day of January, 1989

Attest:

DONALD J. QUIGG

Attesting Officer

Commissioner of Patents and Trademarks